(12) United States Patent
Gerth et al.

(10) Patent No.: US 10,699,406 B2
(45) Date of Patent: Jun. 30, 2020

(54) DETERMINING A PLANT'S BIOMASS

(71) Applicant: Fraunhofer-Gesellschaft zur Förderung der angewandten Forschung e.V., München (DE)

(72) Inventors: Stefan Gerth, Nürnberg (DE); Norman Uhlmann, Obermichelbach (DE); Joelle Claussen, Nürnberg (DE)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 166 days.

(21) Appl. No.: 15/923,910

(22) Filed: Mar. 16, 2018

(65) Prior Publication Data

US 2018/0211384 A1    Jul. 26, 2018

Related U.S. Application Data

(63) Continuation of application No. PCT/EP2016/072187, filed on Sep. 19, 2016.

(30) Foreign Application Priority Data

Sep. 25, 2015  (DE) .................... 10 2015 218 504

(51) Int. Cl.
*G06T 7/00* (2017.01)
*G01N 23/04* (2018.01)
(Continued)

(52) U.S. Cl.
CPC ............. *G06T 7/0012* (2013.01); *A01G 2/00* (2018.02); *A01G 7/00* (2013.01); *G01G 9/005* (2013.01);
(Continued)

(58) Field of Classification Search
CPC .......... G06T 7/0012; A01G 2/00; A01G 7/00; G01G 9/005; G01N 23/04; G01N 23/083; G01N 33/0098

See application file for complete search history.

(56) References Cited

U.S. PATENT DOCUMENTS 7,278,236 B2    10/2007  McDonald et al.
8,383,888 B1 *  2/2013  DeBolt ................ C12N 9/1059
                                                          435/162

(Continued)

FOREIGN PATENT DOCUMENTS

CN    102589441 A    7/2012
JP    2012083152 A   4/2012
(Continued)

OTHER PUBLICATIONS

H. Strange et al.: "Automatic estimation of wheat grain morphometry from computed tomography data", in: Functional Plant Biology 42 (2014), pp. 452-459 (8 pages).

(Continued)

*Primary Examiner* — David F Dunphy
(74) *Attorney, Agent, or Firm* — Haynes and Boone, LLP

(57) ABSTRACT

A method of determining a plant's biomass includes three steps, namely establishing an X-ray photograph of the plant, establishing an absorption characteristic of the plant in an X-ray photograph, and determining the plant's biomass by means of the absorption characteristic of the plant. Said determining is based on a predetermined relation between a reference absorption characteristic and a reference biomass.

15 Claims, 5 Drawing Sheets

(51) Int. Cl.
*G01N 23/083* (2018.01)
*G01N 33/00* (2006.01)
*G01G 9/00* (2006.01)
*A01G 7/00* (2006.01)
*A01G 2/00* (2018.01)

(52) U.S. Cl.
CPC .......... *G01N 23/04* (2013.01); *G01N 23/083* (2013.01); *G01N 33/0098* (2013.01); *G06T 2207/10116* (2013.01)

(56) References Cited

U.S. PATENT DOCUMENTS

| | | | | |
|---|---|---|---|---|
| 9,945,714 | B1* | 4/2018 | Hartwig | G01G 9/005 |
| 10,379,252 | B2* | 8/2019 | Chen | G01N 23/10 |
| 2002/0168046 | A1* | 11/2002 | Hansen | G01N 23/06 |
| | | | | 378/51 |
| 2011/0135161 | A1* | 6/2011 | Koutsky | A01H 1/04 |
| | | | | 382/110 |
| 2011/0243382 | A1* | 10/2011 | Morton | A61B 6/032 |
| | | | | 382/103 |
| 2015/0293041 | A1* | 10/2015 | Mukaide | G01N 23/207 |
| | | | | 378/64 |
| 2019/0120807 | A1* | 4/2019 | Warner | G01N 33/1813 |

FOREIGN PATENT DOCUMENTS

| WO | WO 2013/101806 A1 | 7/2013 |
|---|---|---|
| WO | WO 2014/100237 A2 | 6/2014 |

OTHER PUBLICATIONS

J. R. Rosell et al.: "A review of methods and applications of the geometric characterization of tree crops in agricultural activities", in: Computers and Electronics in Agriculture, vol. 81, Sep. 2011; XP028442024.

Office Action dated Nov. 26, 2019 issued in the parallel Chinese patent application No. 201680068702.0.

* cited by examiner

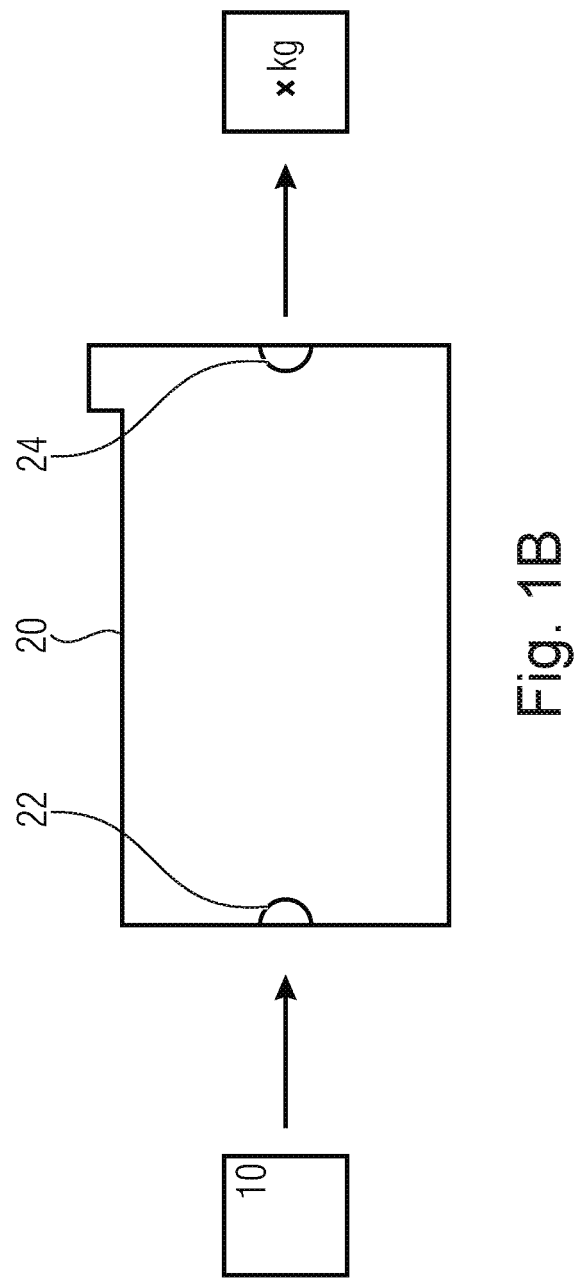

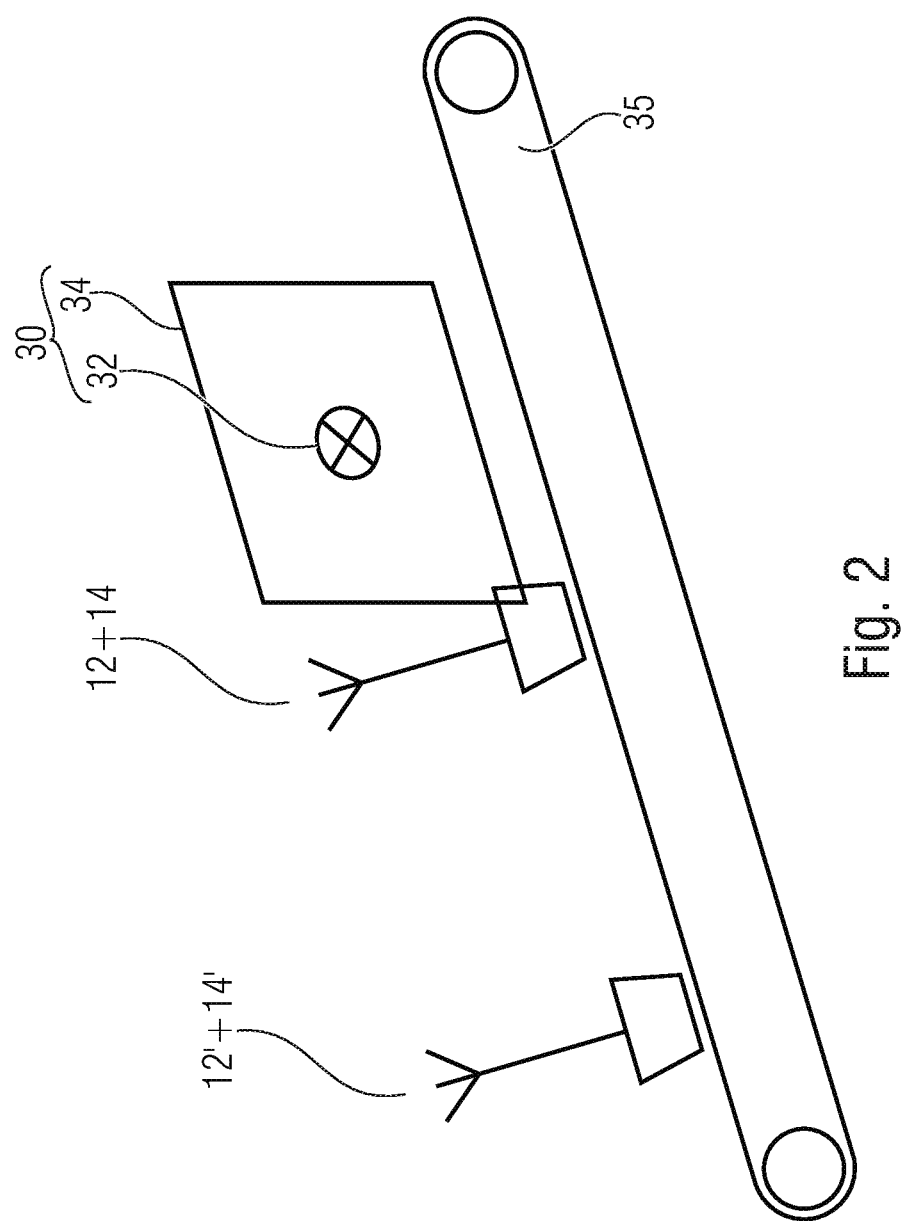

DETERMINING A PLANT'S BIOMASS

CROSS-REFERENCES TO RELATED APPLICATIONS

This application is a continuation of International Application No. PCT/EP2016/072187, filed Sep. 19, 2016, which is incorporated herein by reference in its entirety, and additionally claims priority from German Application No. DE 10 2015 218 504.4, filed Sep. 25, 2015, which is incorporated herein by reference in its entirety.

Embodiments of the present invention relate to a method of determining a plant's biomass, to a corresponding computer program, and to a calculating unit for determining a plant's biomass. Further embodiments relate to a system including the calculating unit for determining the biomass and to an X-ray apparatus as well as to using an X-ray apparatus for determining biomass.

BACKGROUND OF THE INVENTION

For evaluating the potential yield of different phenotypes, biomass is one of the most important features in plant cultivation; however, it is not always readily possible to determine biomass.

One example of determining biomass is to weigh the plant. Weighing of the plant includes one two different variants: for one thing, it is possible to weigh the plant in the greenhouse together with its pot. In this context, differing amounts of watering present in the pot represent a major source of error. In the second variant, the plants are destroyed, and the weight is determined without any interference effects due to the humid soil. Therefore, the method of weighing is either correspondingly imprecise since the humidity of the soil (of the substrate) needs to be determined with high accuracy, or destructive since the plant needs to be cut off and be weighed separately.

A further possibility of determining biomass is the so-called optical method. Here, the plant is optically measured, e.g., by means of a 3D laser cutting method, and the plant's weight is thus approximated. In this case, the level of accuracy of the method is limited by an assumption of thickness and density for the various parts of the plant since it is only the surface of the plant that can be determined by said method. In addition, for various types of plants, it is difficult to optically sense the entire plant due to the interlaced manner in which the plant has grown and to the resulting shading, which results in further inaccuracies.

Therefore, one may state, in summary, that determining of biomass, in particular in field applications, is subject to a certain level of inaccuracy or is invasive, so that weighing cannot be performed until after the harvest. This is why there is a need for an improved approach.

SUMMARY

According to an embodiment, a method of determining biomass of a plant may have the steps of: obtaining an X-ray photograph of the plant; establishing an absorption characteristic of the plant in the X-ray photograph; and determining the biomass of the plant by means of the absorption characteristic of the plant on the basis of a predetermined relation between a reference absorption characteristic and a reference biomass.

According to another embodiment, a non-transitory digital storage medium may have a computer program stored thereon to perform the inventive method, when the program runs on a computer.

Another embodiment may have a calculating unit for determining biomass of a plant, the calculating unit being configured to establish, starting from an obtained X-ray photograph of the plant, an absorption characteristic of the plant in the X-ray photograph and to determine, by means of the absorption characteristic of the plant, the biomass of the plant on the basis of a predetermined relation between a reference absorption characteristic and a reference biomass.

According to another embodiment, a system may have: an inventive calculating unit, and an X-ray apparatus including an X-ray detector and an X-ray source.

Another embodiment may have utilization of an X-ray apparatus for determining biomass of a plant, said determining of the biomass of the plant being effected, by means of an absorption characteristic of the plant, from an X-ray photograph of the X-ray apparatus, and said determining being based on a predetermined relation between a reference absorption characteristic and a reference biomass.

Embodiments of the present invention provide a method of determining biomass which comprises three basic steps. The first step comprises obtaining an X-ray photograph of the plant, the second step comprises establishing an absorption characteristic of the plant in the X-ray photograph, so that a third step comprises being able to determine the biomass of the plant by means of the absorption characteristic of the plant, said determining being based on a predetermined relation between a reference absorption characteristic and a reference biomass.

Therefore, embodiments of the present invention are based on the finding that on the basis of an X-ray photograph of a plant, the biomass may be determined, by means of the weakening of the X-radiation during irradiation, by comparing the weakening which occurs in the radiograph to predetermined occurrences of weakening for which there exist empirically established measured values with regard to the weight and/or the biomass. Thus, a plant's biomass may advantageously be determined in a non-invasive manner and with a very high level of accuracy since said weakening depends on the mass of the body irradiated, or, to be precise, on the density and the volume of the body irradiated (rather than on the shaped surface of the body as is the case, e.g., in optical measurement methods).

In corresponding embodiments, the measurement values may be stored, e.g., a characteristic curve, with at least two predetermined relations of weakening and resulting biomass, or in the form of mathematical mapping, such as linear mapping, for example, or as a simple look-up table comprising a multitude of empirically established and/or interpolated pairs of values. Here it would optionally also be feasible for the formula or characteristic curve or look-up table to apply only to a specific type of plant in each case, so that different behaviors in terms of absorption and biomass may be taken into account.

In accordance with further embodiments, the absorption characteristic may exist as a gray-level image comprising a multitude of gray levels. In this embodiment, the step of determining the plant's biomass would then comprise a difference of establishing an integral across the multitude of gray levels. Thus, the biomass of the entire image content may be advantageously determined by using simple mathematical methods without involving any complicated image processing steps.

In accordance with embodiments, biomass may be determined either in a field, which involves moving the X-ray apparatus used for determining the biomass along the rows of plants, or in the greenhouse. When establishing the biomass of greenhouse plants, the plants concerned are often potted plants, so that in addition to the actual biomass of the plant, the radiograph will also contain the pot which comprises the soil (substrate) surrounding that part of the plant which is located below the soil. In such a case, the method may be configured, in accordance with further embodiments, such that the step of establishing the plant's absorption characteristic takes into account only those parts of the radiographs which concern the parts of the plant which are located above the soil. In accordance with further embodiments, however, it would also be feasible in this context to determine the absorption characteristic of the parts of the plant which are located below the soil so as to thus determine, in a further step, the water content of the (nutrient) medium. This offers the advantage that in addition to the potted plant's actual biomass, it is also possible to determine information regarding the soil moisture.

In accordance with further embodiments, it is also possible, e.g., when using the above-explained method in a field or when using a conveyer belt by means of which the potted plants are made to pass the X-ray apparatus, for a situation to arise wherein several X-ray photographs of plants are taken. In this embodiment, the steps of the method may thus be repeated for a multitude of plants.

In accordance with further embodiments, the method may also include further method steps of a method of establishing the relation between a reference absorption characteristic and a reference biomass. To this end, at least two radiographs are taken of plants of a first type which have different masses, and the associated mass is established, e.g., by weighing, so as to provide, in a subsequent step, association of the respective mass and the absorption characteristic, which then results in the at least two points on the respective characteristic curve. Here it would also be feasible for said two points to be supplemented by further points by means of interpolation.

In accordance with further embodiments, the method may also be partly or fully implemented in the computer program.

Further embodiments relate to a calculating unit for determining the biomass of a plant which is configured to establish, starting from an obtained X-ray photograph of the plant, an absorption characteristic of the plant by means of an X-ray photograph and to determine, by means of the absorption characteristic of the plant, the biomass of the plant on the basis of a predetermined relation between a reference absorption characteristic and a reference biomass.

In accordance with further embodiments, said calculating unit may also be integrated into a system which includes an X-ray apparatus with an X-ray detector and an X-ray source. In this context, the X-ray apparatus may optionally also be configured to establish several photographs while the X-ray apparatus is moving through a field.

An additional embodiment relates to utilization of an X-ray apparatus for determining a plant's biomass.

BRIEF DESCRIPTION OF THE DRAWINGS

Embodiments of the present invention will be detailed subsequently referring to the appended drawings, in which:

FIG. 1B shows a calculating unit for determining a plant's biomass in accordance with a further embodiment;

FIG. 2 shows a system including an X-ray apparatus by means of which the biomasses of potted plants can be determined in accordance with extended embodiments.

DETAILED DESCRIPTION OF THE INVENTION

Figure 1A:
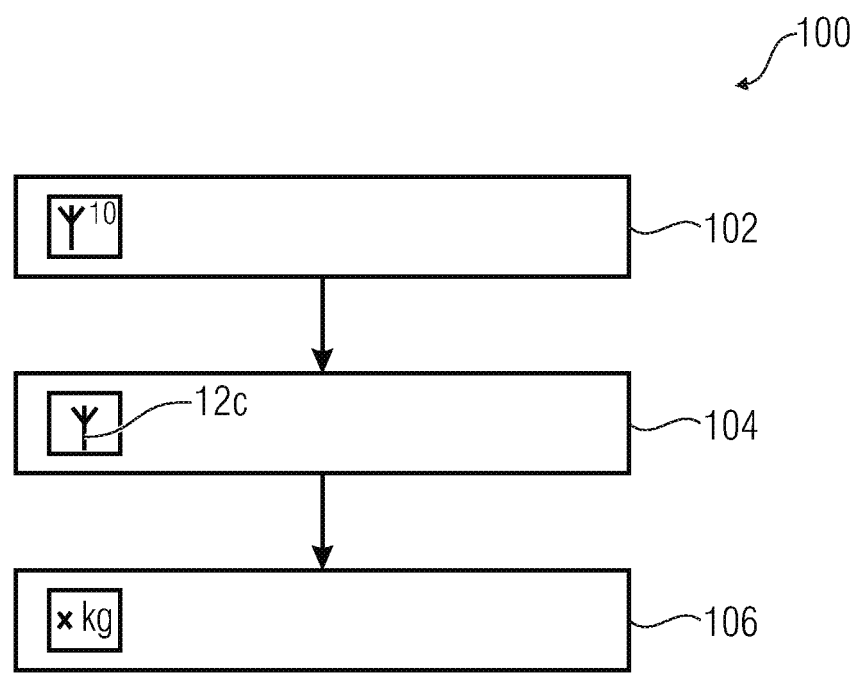
FIG. 1A shows a method of determining a plant's biomass in accordance with a first embodiment.

Before embodiments of the present invention will be explained by means of the figures, it shall be noted that identical elements and structures are provided with identical reference numerals, so that their descriptions are mutually applicable and/or interchangeable.

Figure 1C:
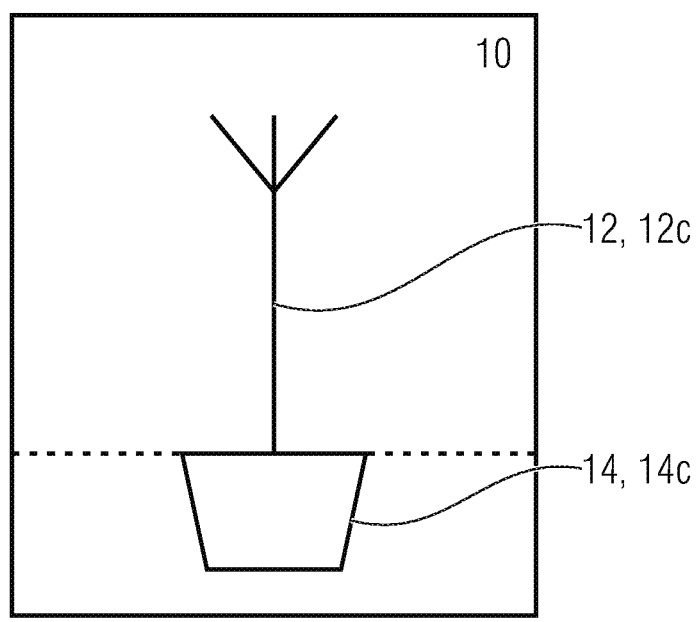
FIG. 1C shows an X-ray photograph of a plant for explaining determining of the biomass.

FIG. 1 shows the method 100 of determining biomass. The method 100 includes the three basic steps 102a, 104 and 106, which will be explained below with reference to FIG. 1C.

The first step 102 comprises obtaining the X-ray photograph 10 (cf. FIG. 1C) of a plant 12, e.g., of corn, wheat, barley or any other (useful) plant. The X-ray photograph 10 is typically a gray-level image which comprises a gray level which is associated with each pixel and which may be associated with a specific level of absorption. The lower the gray level, the higher the level of absorption that has taken place, and/or the more material is irradiated with the X-radiation.

Consequently, in those areas where several layers, or a large amount of mass, are irradiated, the plant 12 will have a darker gray level than in those areas where the concentration of mass is smaller, or where no plant is irradiated. In other words, if the X-radiation penetrates an object, or the plant 12, the X-radiation will be weakened, in accordance with Lambert-Beer law, as a function of the X-ray energy, the depth of irradiation as well as of the density and atomic number of the material to be penetrated by the radiation. If the various parameters (e.g., material and energy) are known, the product of depth and density may be determined, along the path of the X-radiation, by measuring the transmitted intensity behind the object.

On the basis of the above correlation, a second step 104 then comprises establishing the absorption characteristic $12c$ of the plant 12 in the X-ray photograph 10. In this context, the weakened intensity corresponds to the gray-level information of a calibrated X-ray apparatus detector.

Now a third step 106 comprises determining the biomass of the plant 12 by means of the absorption characteristic $12c$. On the basis of a known absorption/mass characteristic curve or value it is possible to determine the biomass, e.g., in kg, from the radiographic image 10 (including the gray-level information established by means of the detector). In this context, what is established in particular is the so-called "fresh weight", i.e., the biomass including water entrapments.

Since constituents of plants differ only to a very small degree in terms of their physical set-up, the absorption/mass characteristic curves of different types of plants are often very similar, so that in a first approximation in accordance with embodiments, a universally applicable characteristic curve may be used. This is to be seen against the background that almost all plants consist of water/carbon compounds.

Said method step 106 first and foremost represents a calculation which may be performed by the calculating unit 20 of FIG. 1B. Said calculation is based, in particular, on the fact that the absorption characteristic $12c$, or an absorption value per pixel, is compared to a previously measured absorption characteristic or to a relation between a reference absorption characteristic and a reference biomass, so that it is possible to draw conclusions as to the biomass of the plant 12.

The absorption characteristic is, e.g., a surface area (projection surface of the plant 12 in the X-ray image 10) comprising different absorption values per point of the surface; the biomass may alternatively also be established per pixel, so that in evaluating the absorption characteristic with regard to the biomass, said biomass will be obtained as a function of the surface area and/or of the extension of growth or height of growth.

For example, a value which initially is non-dimensional, or a volume value for the plant may also be established by summing up/integrating all of the gray levels of the individual pixels. Said value may then be compared to a stored value, or a stored reference relation. The stored relation may be present, e.g., as a characteristic curve, as a mathematical function, or as a simple look-up table.

Said establishing of the relation is possible by means of an additional method, which may be combined with the method 100. Moreover, said establishing may also be effected by means of the calculating unit 20. To perform said establishing, at least two plants of different masses are measured and/or weighed, and the associated absorption characteristics are determined experimentally, so that one now obtains two local relations between the mass and the associated absorption characteristic. On the basis of these two points, interpolation and/or extrapolation of third values may be effected, so that the relation exists across a broad range of mass and absorption characteristic. By calibrating the detector in this manner, the correlations between mass and gray levels for different plants or the correlations between water content and gray levels for different soil compositions are stored. As was already indicated, the calibration method may, in accordance with further embodiments, be part of the method 100 or be part of the range of functions of the calculating unit 20.

In accordance with further embodiments it shall be noted that in particular in the event that the plant 12 exists as a plotted plant, the X-ray photograph 10 frequently also images the pot 14 with the soil 14 (e.g., the earth 14) contained therein and the root of the plant 12. In such embodiments it is advantageous for the method to include differentiation between those parts of the plant 12 which are located above and below the soil, or, generally, above and below the substrate surface, respectively. Also, in accordance with further embodiments, the method may include the step of establishing the absorption characteristic 12c above the earth, so that on the basis thereof, the biomass of the plant 12 is determined. In addition, the method may optionally also include the step of establishing the absorption characteristic 14c below the soil since said absorption characteristic 14c may be used as the basis for establishing, in particular, the water content of the soil contained within the pot 14. The water content of the soil allows a conclusion to be drawn in terms of the soil moisture and the watering behavior associated therewith.

With reference to FIG. 1C and to the absorption characteristics 12c and 14c it shall be noted that in principle, the absorption characteristic is dependent on three factors for each radiation point. Said three factors include the volume along the irradiation direction, the density within said volume, and an absorption constant, which may differ for different materials and, therefore, also for different plants. This is why in accordance with further embodiments, a predetermined relation between the reference mass and the reference absorption characteristic, which includes said very factor which is specific to the irradiation object, may be stored, or the factor which is dependent on the irradiation material may be directly taken into account in calculating the absorption characteristic and/or in subsequent calculation of the biomass.

Figure 3:
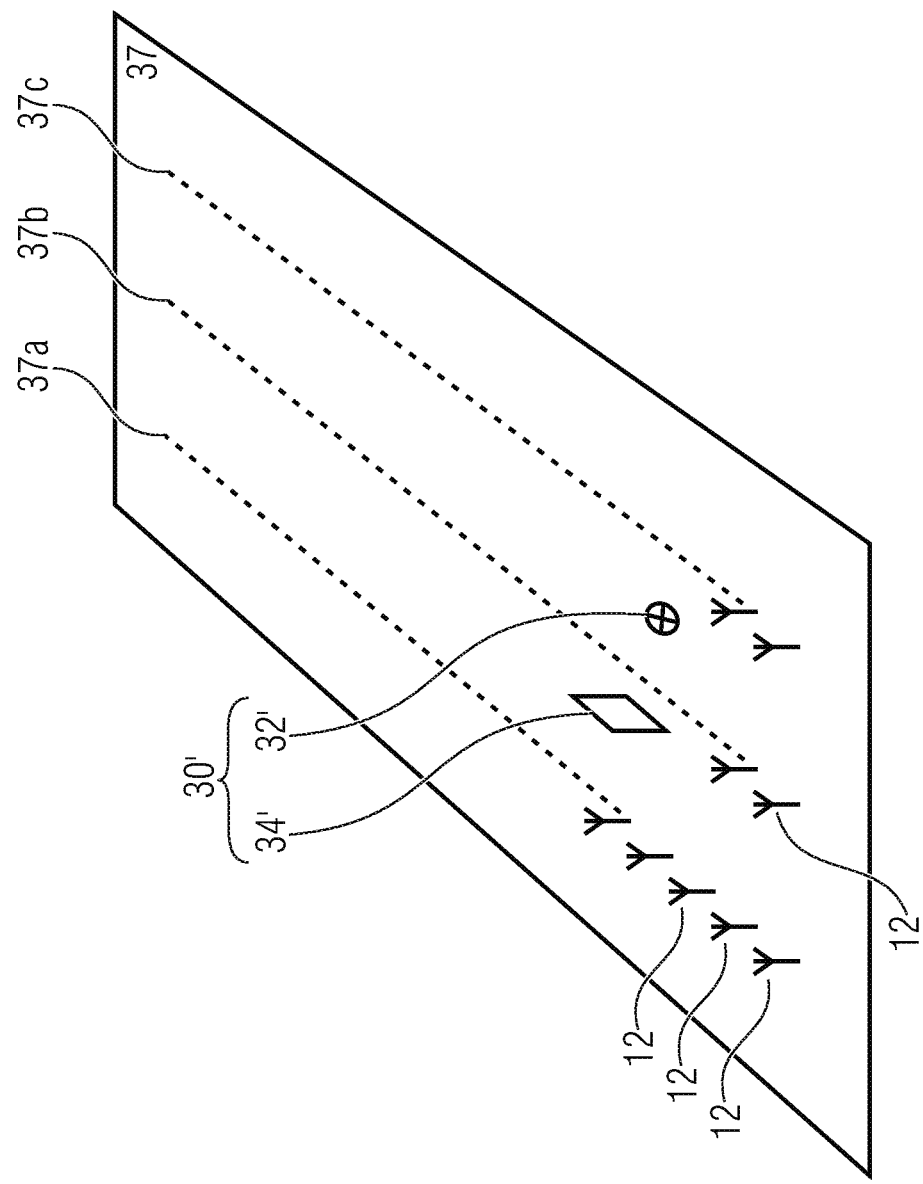
FIG. 3 shows a system including an X-ray apparatus by means of which the biomasses of plants can be determined in a field, in accordance with extended embodiments.

In accordance with further embodiments, the calculating unit 20 may be connected to an X-ray apparatus via its interface 22 for receiving the one or more X-ray photographs and via its interface 14 (e.g., user interface, display), as depicted in FIGS. 2 and 3.

FIG. 2 shows an X-ray apparatus 30 comprising an X-ray tube 32 and an X-ray detector 34 such as a line or area detector, for example. In this embodiment, the X-ray apparatus 30 is combined with the conveyer belt 35 to form a conveyer-belt system.

As can be seen, the conveyer belt 35 has a series of potted plants 12' plus 14' and/or 12 plus 14, respectively, arranged thereon, which are consecutively x-rayed by means of the X-ray apparatus 30 when the plants are moved between the X-ray tube 32 and the X-ray detector 34 with the aid of the conveyer belt 35. Thus, for each plant 12 or 12', a corresponding X-ray photograph is obtained so as to then determine the respective biomass in one of the subsequent steps. By analogy therewith, it is also possible to determine the relative moisture of the soil contained within the pot 14 and/or 14' as explained above. In other words, this means that it is possible to both evaluate various parts (the plant's biomass as a function of the height of growth or the water content of the pot) and the integral biomass of that part of the plant which is located above the soil. Said variant comprising the conveyer belt 35 is suitable, in particular, for plant or agricultural cultivation in greenhouses since here the plants 12 or 12' are typically present in pots 14 and 14'.

It shall be noted at this point that the above-explained method steps of the method 100 are consecutively performed for each plant pot combination 12 plus 14 and 12' plus 14', respectively. In addition, it is also possible to evaluate a sequence of X-ray photographs which will then image several plants, or several parts of plants, when, e.g., the X-ray photographs are continuously taken while the conveyer belt 35 is moving at the same time. In accordance with embodiments, it is reasonable, in this case, to employ image processing which in X-ray images associates the imaged parts with the various plants so as to then determine the biomass for each individual plant separately. Said image processing may be based, for example, on the fact that marginal areas of a plant culture are detected, e.g., on the basis of low absorption rates in said areas. Here it is also possible to use image processing by means of which those areas of the pot and of the plant which are located above the soil line are separated from one another.

With reference to FIG. 3, a further embodiment shall be explained wherein the above method is employed in a field. Here, a mobile X-ray apparatus 30' comprising a mobile X-ray detector 34' and a mobile X-ray tube 32' is depicted.

In this embodiment, too, the X-ray tube 32' and the X-ray detector 34' are arranged opposite the plants 12 in such a manner that the latter are X-rayed. This means, therefore, that the plants 12 which are cultivated in lines 37a to 37c in the field 37 will be located between the X-tube 32' and the X-ray detector 34' during X-raying. This may be ensured, for example, in that the X-ray tube 32' is moved through the field, in parallel with the X-ray detector 34', in the intermediate zone located between rows 37a and 37b, while the X-ray detector 34' is moved through the field in the intermediate zone located between the rows 37b and 37c. Alternatively, it would also be feasible for the detector 34' and the X-ray tube 32' to be moved through the field 37 together, e.g., by means of a bridge arranged above the plant 12. Determining of the biomass corresponds to the above procedure, it being noted that in the embodiment, it is essentially only possible to determine, in the field 37, the biomasses of the plants 12; determining of the water content of the soil is advantageously implementable by means of conventional moisture sensors.

Further embodiments relate to utilization of an X-ray apparatus for determining the biomass, wherein the above-explained method 100 or the above-explained calculating unit 20 is employed. Said utilization is advantageous since, as was essentially explained above, the biomass may be determined in a fast, uncomplicated and trouble-free manner.

Even though the above embodiments were based on the assumption that the plants 12 to be X-rayed are X-rayed one after the other and that, therefore, a two-dimensional projection of the "row of plants" results, it shall be noted at this point that in accordance with further embodiments, it is also possible to perform different projections of different X-raying angles per plant 12 so as to obtain improved determining of the biomass for each plant 12, e.g., via the intermediate step of a three-dimensional model.

Even though in above embodiments, some aspects have been described within the context of a device, it is understood that said aspects also represent a description of the corresponding method, so that a block or a structural component of a device is also to be understood as a corresponding method step or as a feature of a method step. By analogy therewith, aspects that have been described in connection with or as a method step also represent a description of a corresponding block or detail or feature of a corresponding device. Some or all of the method steps may be performed by a hardware device (while using a hardware device), such as a microprocessor, a programmable computer or an electric circuit. In some embodiments, some or several of the important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or actually do cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. Said transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware specific to the method, such as an ASIC.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A method of determining biomass of a plant, comprising:
    acquiring an X-ray photograph of the plant;
    establishing an absorption characteristic of the plant in the X-ray photograph;
    determining the biomass of the plant by means of the absorption characteristic of the plant on the basis of a predetermined relation between a reference absorption characteristic and a reference biomass wherein the X-ray photograph comprises the parts of the plant which are located above and below the substrate surface, the plant being surrounded by a substrate below the substrate surface, and the method performing establishing the absorption characteristic of the plant in the X-ray photograph only for that part of the plant which is located above the substrate surface.

2. The method as claimed in claim 1, the method further comprising establishing an absorption characteristic of the substrate surface together with that part of the plant which is located below the substrate surface in the X-ray photograph, and the method further comprising determining the water content of the substrate.

3. The method as claimed in claim 1, wherein the absorption characteristic of the plant exists as a gray-level image comprising a multitude of gray levels, and
wherein said determining of the biomass of the plant by means of the absorption characteristic comprises establishing an integral across the multitude of gray levels.

4. The method as claimed in claim 1, the method being repeated for a multitude of plants, said multitude of plants being established by means of several X-ray photographs acquired during a relative movement between a plant and an X-ray apparatus.

5. The method as claimed in claim 4, wherein the relative movement results from a movement of the plant in relation to the X-ray apparatus, which movement is generated by a conveyer belt for conveying the plant.

6. The method as claimed in claim 4, wherein the movement between a plant and the X-ray apparatus results from a movement of the X-ray apparatus through a field of plants planted in a linear manner.

7. The method as claimed in claim 1, wherein the relation between a reference absorption characteristic and a reference biomass is represented in a characteristic curve or is stored by means of a look-up table or may be calculated by means of a formula.

8. The method as claimed in claim 7, wherein the formula, the characteristic curve and/or the look-up table in each case is established for a specific type of plant.

9. The method as claimed in claim 1, comprising the method of determining the relation between the reference absorption characteristic and the reference biomass,
the method of determining the relation comprising:
acquiring an X-ray photograph of a plant of a first type which exhibits a first mass;
acquiring an X-ray photograph of a plant of the first type which exhibits a second mass;
establishing a reference absorption characteristic of the plant which exhibits the first mass in the X-ray photograph;
establishing a reference absorption characteristic of the plant which exhibits the second mass in the X-ray photograph;
weighing the plant which exhibits the first mass so as to acquire a reference biomass of the plant which exhibits the first mass;
associating the reference absorption characteristic of the plant which exhibits the first mass with the corresponding reference biomass so as to acquire a first local relation;
weighing the plant which exhibits the second mass so as to acquire a reference biomass of the plant which exhibits the second mass; and
associating the absorption characteristic of the plant which exhibits the second mass with the corresponding reference biomass so as to acquire a second local relation,
wherein the relation between the reference absorption characteristic and the reference biomass may be determined by means of the first and second local relations.

10. The method as claimed in claim 9, further comprising interpolating and/or extrapolating between the first and the second local relations so as to establish a third local relation.

11. A non-transitory digital storage medium having a computer program stored thereon to perform a method of determining biomass of a plant, said method comprising:
acquiring an X-ray photograph of the plant;
establishing an absorption characteristic of the plant in the X-ray photograph; and
determining the biomass of the plant by means of the absorption characteristic of the plant on the basis of a predetermined relation between a reference absorption characteristic and a reference biomass,
wherein the X-ray photograph comprises the parts of the plant which are located above and below the substrate surface, the plant being surrounded by a substrate below the substrate surface, and
the method performing establishing the absorption characteristic of the plant in the X-ray photograph only for that part of the plant which is located above the substrate surface
when the program runs on a computer.

12. A calculating unit for determining biomass of a plant, the calculating unit being configured to establish, starting from an acquired X-ray photograph of the plant, an absorption characteristic of the plant in the X-ray photograph and to determine, based on the absorption characteristic of the plant, the biomass of the plant on the basis of a predetermined relation between a reference absorption characteristic and a reference biomass;
wherein the X-ray photograph comprises the parts of the plant which are located above and below the substrate surface, the plant being surrounded by a substrate below the substrate surface, and
wherein the absorption characteristic of the plant in the X-ray photograph only for that part of the plant which is located above the substrate surface.

13. A system comprising the calculating unit as claimed in claim 12, and
an X-ray apparatus comprising an X-ray detector and an X-ray source.

14. A system comprising a calculating unit for determining biomass of a plant, the calculating unit being configured to establish, starting from an acquired X-ray photograph of the plant, an absorption characteristic of the plant in the X-ray photograph and to determine, based on the absorption characteristic of the plant, the biomass of the plant on the basis of a predetermined relation between a reference absorption characteristic and a reference biomass, and
an X-ray apparatus comprising an X-ray detector and an X-ray source wherein the X-ray apparatus is configured to establish several X-ray photographs during movement of the X-ray apparatus through a field.

15. A method of using an x-ray apparatus to determine a biomass of a plant, the method comprising:
determining the biomass of the plant of based on an absorption characteristic of the plant, from an X-ray photograph of the X-ray apparatus, and said determining being based on a predetermined relation between a reference absorption characteristic and a reference biomass;
wherein the X-ray photograph comprises the parts of the plant which are located above and below the substrate surface, the plant being surrounded by a substrate below the substrate surface, and wherein the absorption characteristic of the plant in the X-ray photograph only for that part of the plant which is located above the substrate surface.

* * * * *